United States Patent [19]

Persidsky

[11] Patent Number: 4,828,557

[45] Date of Patent: May 9, 1989

[54] STERILE CONNECTOR AND METHOD

[76] Inventor: Maxim D. Persidsky, 35 Temescal Ter., San Francisco, Calif. 94118

[21] Appl. No.: 597,545

[22] Filed: Apr. 6, 1984

[51] Int. Cl.⁴ ............................................. A61M 5/00
[52] U.S. Cl. .................................................... 604/408
[58] Field of Search ...................... 604/283, 410, 905; 285/3

[56] References Cited

U.S. PATENT DOCUMENTS

| | | | |
|---|---|---|---|
| 3,968,195 | 7/1976 | Bishop | 604/410 |
| 4,022,256 | 5/1977 | Berkman et al. | 141/1 |
| 4,157,723 | 6/1979 | Granzow et al. | 285/3 |
| 4,265,280 | 5/1981 | Ammann et al. | 285/3 |
| 4,325,417 | 4/1982 | Boggs et al. | 285/3 |
| 4,340,097 | 7/1982 | Ammann et al. | 285/3 |
| 4,368,729 | 1/1983 | Dossin | 604/410 |
| 4,369,779 | 1/1983 | Spencer | 604/905 |
| 4,412,835 | 11/1983 | Spencer | 604/905 |
| 4,434,822 | 3/1984 | Bellamy et al. | 604/7 |

OTHER PUBLICATIONS

*Development and Fabrication of an Aseptic Fluid Transfer System,* (AFTS), Richard M. Berkman et al., Report No. 5040-7, Jet Propulsron Laboratory, Sep. 20, 1975.
*An Improved Aseptic Fluid Transfer System (AFTS),* Berkman et al., Report No. 5040-7 Supplement, Jet Propulsion Laboratory, Oct. 31, 1975.
Dhew Pub. #(NiH) 76-1004, "Frozen Red Cell Outdating", Mar. 14, 1975, Edited by Sherer.

*Primary Examiner*—C. Fred Rosenbaum
*Attorney, Agent, or Firm*—Flehr, Hohbach, Test, Albritton & Herbert

[57] ABSTRACT

Connector and method for joining two conduits together in a sterile manner permitting aseptic fluid transfer between axially extending passageways in the conduits. End caps fabricated of a material which melts and flows at a sterilizing temperature are connected to the terminal ends of the conduits and brought together within an outer sleeve. Heat is applied to the sleeve to melt the plastic material and cause it to flow out of the region between the passageways, thereby providing communication between the passageways and conding the conduits together in a sterile manner.

14 Claims, 1 Drawing Sheet

U.S. Patent     May 9, 1989     4,828,557
Fig.1
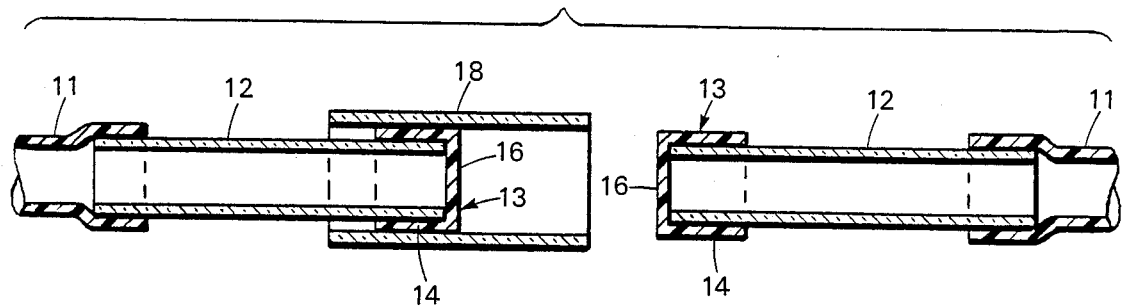
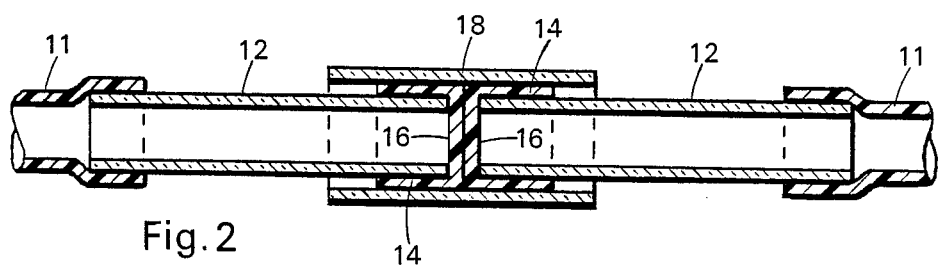
Fig. 2
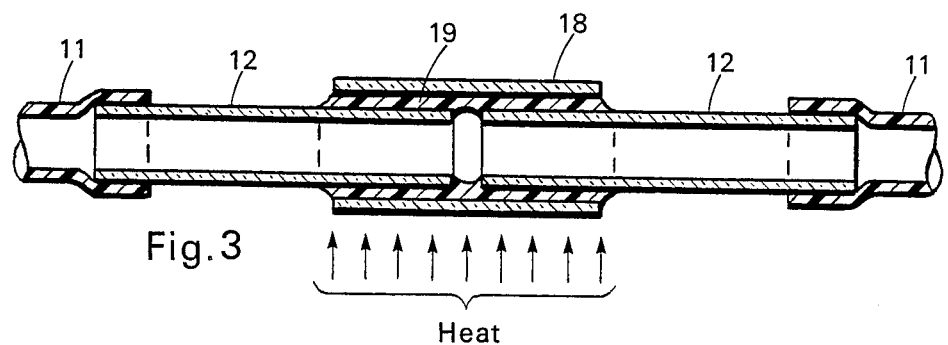
Fig. 3
Heat

STERILE CONNECTOR AND METHOD

This invention pertains to a connector and method for joining two conduits together in a sterile manner to permit aseptic fluid transfer between the conduits.

In the medical field, and in other fields, it is often necessary to transfer fluids between two closed systems without contamination by any extraneous matter including microbial bacteria and airborne contaminants. This need arises, for example, in the handling of blood and its components, as well as in other medical situations such as attachments to heart-lung machines and kidney-dialysis machines.

Heretofore, there have been numerous attempts to provide sterile connections, but these prior attempts have been subject to certain limitations and disadvantages such as complexity and cost, impeded flow between the two systems, and less than complete absence of contamination. Examples of such prior techniques are found in U.S. Pat. Nos. 3,865,411, 3,909,910, 4,022,256, 4,157,723, 4,187,846, 4,265,280, 4,325,417 and 4,340,097.

It is in general an object of the invention to provide a new and improved sterile connector and method for joining two conduits together to permit aseptic fluid transfer between the conduits.

Another object of the invention is to provide a connector and method of the above character which overcome the limitations and disadvantages of sterile connectors heretofore provided.

Another object of the invention is to provide a connector and method of the above character which are economical and easy to use.

These and other objects are achieved in accordance with the invention by providing the terminal ends of the conduits to be connected together with end caps of a material which melts and flows at a sterilizing temperature. These end caps are inserted into a sleeve, with the passageways in the conduits aligned axially and the end walls of the caps facing each other in confronting relationship. The end caps and the sleeve are heated to the sterilizing temperature to melt the end caps and draw the material from the end walls out of the region between the passageways. The molten material cools and hardens to form a permanent bond between the conduits.

FIG. 1 is a centerline sectional view of one embodiment of a sterile connector according to the invention, with the parts separated prior to connection.

FIG. 2 is a view similar to FIG. 1, with the parts in position to be bonded together.

FIG. 3 is a view similar to the other figures, with the parts bonded together and communication established between the conduits thus connected.

In the drawings, the invention is illustrated in connection with a pair of conduits 11 in the form of flexible plastic tubes connected to sterile containers (not shown) such as blood bags. Rigid tubular members 12 are connected to the terminal ends of the flexible tubes in a fluid-tight manner, for exampmle by stretching the end portions of the tubes over the tubular members. End caps 13 having side walls 14 and end walls 16 are mounted on the free ends of the tubular members to seal the containers at the terminal ends of the tubes. A rigid cylindrical sleeve 18 is fitted over one of the tubular members with the side wall of the end cap being positioned between the outer wall of the tubular member and the inner wall of the sleeve. The sleeve is about three times as long as the side wall of the end cap, and it projects axially from the tubular member on which it is mounted to receive the other tubular member in a like manner when the parts are joined together.

End caps 13 are fabricated of a thermoplastic material which melts and flows at a sterilizing temperature which is sufficient high to kill thermophilic bacteria. The sterilizing temperature is preferably on the order of 300° C. or more, and one suitable material for the end caps is polyethylene. Tubular members 12 and outer sleeve 18 are fabricated of a material which does not melt at the sterilizing temperature, and it is also preferable that these parts to be fabricated of a material which is transparent to gamma rays commonly used in the sterilization of medical appliances. In one presently preferred embodiment, the tubular members and the sleeve are fabricated of Pyrex glass.

Operation and use of the connector, and therein the method of the invention are as follows. Prior to being joined together, end caps 13 seal the containers and conduits to which they are connected. To join the conduits together, the free ends of tubular members 12 are inserted into sleeve 18, with the flow passageways in the tubes being aligned axially and the end walls of the end caps facing each other in confronting relation within the sleeve. Prior to connection, sleeve 18 can either be attached to one of the tubular members or it can be kept separately and installed on both of the tubular members at the time of connection. with both of the tubular members inserted into the sleeve, the connection is made by applying heat to the outer surface of the sleeve to melt the plastic caps therein. The molten plastic from the end walls of the caps flows out of the region between the passageways in the tubular members and is drawn by capillary action into the region between the outer walls of the tubular members and the inner wall of the sleeve, thereby opening the passageway between the two conduits. The plastic material from the end walls combines with the plastic material from the side walls of the end caps, and the mass of plastic material 19 bonds the tubular members and the sleeve together as it cools and hardens, thereby joining the two conduits together in a permanent manner. The melting and flowing of the plastic material also serves to kill any bacteria which may be present on the outer surface of the end caps. The sterilizing temperature kills the bacteria, and any contamination on the end walls becomes embedded in the molten plastic and is carried out of the passageway formed between the tubes.

In applications where the conduits to be joined together are fabricated of a material which does not melt at the sterilizing temperature, tubular members 12 can be omitted, and end caps 13 can be mounted directly on the free ends of the conduits, in which case the ends of the conduits themselves are inserted into sleeve 18 to form the connection.

The invention has a number of important features and advantages. It is economical and easy to use. The passageways in the conduits which are joined together are aligned axially of each other to provide a substantially less impaired flow than prior art connectors in which the passageways are offset and the connection is made through a side wall. In addition, the melting and flowing of the plastic end caps serves to kill bacteria and to embed contaminants in the melted plastic and carry the embedded contaminants away from the sterile passageway of the connector.

It is apparent that a new and improved connector and method have been provided for joining conduits together in a sterile manner to permit aseptic fluid transfer between the conduits. While only certain presently preferred embodiments have been described in detail, as will be apparent to those familiar with the art, certain changes and modfications can be made without departing from the scope of the invention as defined by the following claims.

I claim:

1. In a connector for joining two conduits together in a sterile manner permitting aseptic fluid transfer between axially extending passageways in the conduits: end caps connected to the terminal ends of the conduits for sealing the passageways before the conduits are joined together, said end caps having end and side walls fabricated of a material which melts and flows at a sterilizing temperature, and a sleeve which fits over the end caps with the passageways aligned axially and the end walls of the caps facing each other in confronting relation, the material forming the end caps flowing by capillary action out of the region between the passageways and into the region between the conduits and the sleeve to bond the conduits and the sleeve together and provide a connection between the passageways when the end caps are melted.

2. The connector of claim 1 wherein the end caps are fabricated of a thermoplastic material.

3. The connector of claim 2 wherein the end caps are fabricated of polyethylene.

4. The connector of claim 1 wherein the sleeve is fabricated of a material which is transparent to gamma rays.

5. The connector of claim 4 wherein the sleeve is fabricated of glass.

6. The connector of claim 1 wherein the end caps are mounted on rigid tubular members of smaller diameter than the sleeve, with the side walls of the end caps being positioned between the outer walls of the tubular members and the inner wall of the sleeve.

7. The connector of claim 6 wherein the tubular members are fabricated of a material which is transparent to gamma rays.

8. The connector of claim 7 wherein the tubular members are fabricated of glass.

9. Aseptic fluid storage and transfer apparatus, comprising first and second sterile containers each having a closed chamber for holding a fluid and a flexible tube with an axially extending passageway in fluid communication with the chamber, a pair of glass tubular members each connected at one end to the terminal end of one of the flexible tubes, end caps having end and side walls fabricated of a thermoplastic material which melts and flows at a sterilizing temperature mounted on the free ends of the tubular members to seal the containers and the ends of the tubes, and a glass sleeve mounted coaxially on one of the tubular members and extending axially therefrom for receiving the other tubular member in a like manner with the side walls of the end caps being positioned between the outer walls of the tubular members and the inner wall of the sleeve and the end walls of the caps facing each other in confronting relations within the sleeve, the plastic material forming the end walls flowing by capillary action out the region between the confronting ends of the tubular members and into rhe region between the outer walls of the tubular members and the inner wall of the sleeve to thereby bond the tubular members together and provide communication between passageways when the plastic material is heated to the sterilizing temperature and is melted.

10. The apparatus of claim 9 wherein the thermoplastic material has a melting temperature of at least 300° C.

11. The apparatus of claim 10 wherein the end caps are fabricated of polyethylene.

12. The apparatus of claim 9 wherein the tubular members and the sleeve each have a generally cylindrical outer contour.

13. In a method of joining two conduits together in a sterile manner permitting aseptic fluid transfer between axially extending passageways in the conduits, the steps of: connecting end caps with end and side walls fabricated of a material which melts and flows at a sterilizing temperature to the terminal ends of the conduits, inserting the end caps into a sleeve with the passageways aligned axially and the end walls of the conduits facing each other in confronting relation, heating the end caps and the sleeve to the sterilizing temperature to melt the end caps and by capillary action draw the material from the end caps out of the region between the passageways and into the region between the conduits and the sleeve, and cooling the melted material within the sleeve to bond the conduits and the sleeve together to provide a secure and permanent joint between the two conduits with an unimpaired passageway.

14. The method of claim 13 including the steps of connecting rigid tubular members to the terminal ends of the conduits, and mounting the end caps on the tubular members.

* * * * *